United States Patent [19]

Tiburtius

[11] Patent Number: 5,086,061
[45] Date of Patent: * Feb. 4, 1992

[54] USE OF BETA BLOCKERS FOR THE TREATMENT OF THE PROGRESSION OF INFANTILE AXIAL MYOPIA

[75] Inventor: Heinfried Tiburtius, Berlin, Fed. Rep. of Germany

[73] Assignee: Dr. Gerhard Mann Chem.-Pharm. Fabrik GmbH, Berlin, Fed. Rep. of Germany

[*] Notice: The portion of the term of this patent subsequent to Jul. 17, 2007 has been disclaimed.

[21] Appl. No.: 505,432

[22] Filed: Apr. 9, 1990

Related U.S. Application Data

[63] Continuation-in-part of Ser. No. 315,096, Feb. 24, 1989, Pat. No. 4,942,161.

[30] Foreign Application Priority Data

Feb. 25, 1988 [DE] Fed. Rep. of Germany ....... 3805882

[51] Int. Cl.$^5$ .................... A61K 31/47; A61K 31/34; A61K 31/135
[52] U.S. Cl. .................................. 514/309; 514/469; 514/646
[58] Field of Search ............... 514/717, 730, 646, 309, 514/469

*Primary Examiner*—Frederick E. Waddell
*Assistant Examiner*—Zohreh A. Fay
*Attorney, Agent, or Firm*—Cushman, Darby & Cushman

[57] ABSTRACT

The invention relates to the use of beta blockers for the treatment of the progression of infantile axial myopia.

3 Claims, No Drawings

USE OF BETA BLOCKERS FOR THE TREATMENT OF THE PROGRESSION OF INFANTILE AXIAL MYOPIA

FIELD OF THE INVENTION

Cross reference to related application

This is a continuation-in-part of application Ser. No. 07/315,096, filed Feb. 24, 1989, now U.S. Pat. No. 4,942,161.

The invention relates to the use of beta blockers for the treatment of the progression of infantile axial myopia.

BACKGROUND OF THE INVENTION

Myopia or shortsightedness is a disease of the eye in which parallel entering rays of light coverage in front of the retina. It is possible for this desease to have two entirely different causes, namely either that the refraction of the rays in the eye is too strong, such as occassionally occurs in diabetics as well as during the onset of certain types of gray cataracts, which is then called curvature myopia, or because the eyeball is too long, resulting in so-called axil myopia, which is partially hereditary. The only therapy known up to now in the case of axial myopia is the use of concave spectacle lenses, which shift the focus back onto the retina, or of contact lenses, which are intended to slow the increase in length mechanically by exerting pressure on the eye.

Infantile axial myopia arises in most cases at school age between nine and eleven years of age, seldom earlier than that, and as a rule increases until approximately sixteen years of age. The causes of teh disease are not definitely known, although an increas in shortslightedness has been noted. With the end of the period of growth of children, i.e. around the age of sixteen, the covers of teh bulbus oculi, which were soft up to that time, have strengthened to a degree that further longitudinal increase of the eyeball, which would be equivalent to an increase in shortsightedness, is as a rule not expected.

However, there are relatively rare cases of congenital glaucoma in which the eye pressure is already greatly elevated at age one or two. If this pressure cannot be normalized, it expands the eyeball in balloon-like fashion. The afflicted child becomes extremely shortsighted and may finally become blind because of the destruction of the optical nerves. In contrast to this is the fact that if the internal pressure in the eye is increased in adults, that is, by glaucoma, shortsightedness is not triggered, since glaucoma hardly occurs before the age of forty, when the bulbus oculi covers are strong enough so that shortsightedness no longer develops.

Present standard therapy for the treatment of glaucoma consists in the administration of beta blockers which originally have been used in coronary or circulatory therapy. Not only are beta blockers capable of reducing increased blood pressure, they can also normalize the increased internal eye pressure by blocking the production of aqueous humor. For example, the use of beta blockers in myopia caused by glaucoma has been described in *DAZ* No. 16 of Apr. 19, 1984, pp. 281-287. As a rule, beta blockers are used in the form of isomer mixtures, however, it has been found lately that in some cases the antipodes are effective in different ways; in most cases the levorotating antipodes are beta-sympatholytically active to a larger degree.

It is known that the internal eye pressure, determined by aqueous humor production and discharge, is not pathologically increased in children, and fluctuates in the normal range between 10 and 20 mm/Hg. Completely unexpectedly, it has now been determined that beta blockers are capable of preventing the development and progression of infantile axial myopia if regularly applied in relatively weak doses. No definite explanation of this phenomenon has been possible up to now because, as mentioned, children who develop axial myopia as a rule have normal internal eye pressure.

The usable beta blockers include all substances that have been used up to now in the treatment of glaucoma, such as, for example, methypranol, metrizoranolol, propanolol, alprenolol, oxprenolol, practolol, acebutolol, prindolol, metoprolol, atenolol, sotalol, metindol, nadolol, labetalol, practolol, bunitrolol, hedroxalol, tiprenolol, tomalolol, timolol, celiprolol, mepindolol, indenolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. Also, the following beta blocker compounds may be employed: levobunolol, carteolol, befunolol and betaxolol. The substances can be used as isomers mixtures or in their respective levorotating or dextrorotating form.

As a rule treatment consists of one drop into each eye twice a day, at a beta clocker dosage of from 0.075% to 0.15% solution. This therapy must be regularly followed from the onset, or prior to the onset, of the expected shortsightedness until the end of the growth period of the child, as a rule up to the age of sixteen.

DETAILED DESCRIPTION

The invention will be described in detail below by means of examples.

EXAMPLE 1

Preparation of the Beta Blocker Solution 0.355 kg of 1 N hydrochloric acid are dissolved in 97.25 kg of water for use in injections and then 0.100 kg of metipranolol are added while stirring. To the clear solution are added in succession 0.010 kg of benzalkonium chloride, 0.500 kg of sodium chloride, 0.010of sodium editate, 1.000 kg of 85% glycerol and 1.800 kg of polyvinylpyrrolidone (mean molecular weight 90.000) and are dissolved while stirring. After a clear solution has been formed, the pH value is checked and, if required, is set to pH 5.5 with 1N caustic soda.

The solution is filtered into a receiver sterilized by steam via a 0.2 μm filter sterilized by steam by using nitrogen sterilized by filtration as pressure gas. The solution is then automatically dispensed by laminar flow into sterile containers made of high pressure polyethylene of one ml capacity using sterile caps.

The concentration of the active ingredient is 0.1%.

In a similar manner it is possible to produce solutions of the remaining beta blockers known per se. The pH of the solutions should be set at approximately 5.5 to 6 and the solutions should be kept isotonic by the addition of sodium chloride.

EXAMPLE 2

The effectiveness of the use of beta blockers for the treatment of infantile myopia was clinically tested on groups of 15 children. Originally the children showed continuous increase of shortsightedness. The children were treated twice a day with a drop of a 0.1% aqueous solution of metipranolol in each eye. No side effects of a systemic nature were observed. After every two months the customary tests where performed to determe visual faculty. No progress of the myopia was noted in any of the test subjects. Clinical tests so far have extended over a period of several years, during which no worsening of the visual acuity was noted.

What is claimed is:

1. A method for the prevention or treatment of progressive infantile axial myopia in the presence of normal internal eye pressure comprising the step of administering to the eye of patient an effective amount of an aqueous solution of an ophthalmology acceptable beta blocker selected from the group consisting of levobunolol, carteolol, befunolol and betaxolol in amounts such that on repeated administration essentially no side effects of a systemic nature are observed.

2. The method as claimed in claim 1 wherein said beta blocker is present in an aqueous solution in an amount from about 0.075% to about 0.15%.

3. The method as claimed in claim 2 wherein said beta blocker is present in said aqueous solution in an amount of about 0.1%.

* * * * *